United States Patent [19]
Hazard et al.

[11] Patent Number: 5,511,557
[45] Date of Patent: Apr. 30, 1996

[54] URINE SPECIMEN COLLECTION DEVICE

[76] Inventors: James T. Hazard, 347 Kenwood Way, Louisville, Ky. 40215; R. Vincent Kidd, III, 2101 Robin Ave., Hammond, La. 70401

[21] Appl. No.: 384,125

[22] Filed: Feb. 6, 1995

Related U.S. Application Data

[62] Division of Ser. No. 149,549, Nov. 9, 1993, abandoned.

[51] Int. Cl.[6] ........................................ A61B 5/00
[52] U.S. Cl. ............................................ 128/760; 604/349
[58] Field of Search ........................ 128/760, 763, 128/764, 766, 767; 604/326–330, 347, 349, 351, 352

[56] References Cited

U.S. PATENT DOCUMENTS

| | | |
|---|---|---|
| Re. 26,854 | 4/1970 | Giesy . |
| 1,510,973 | 10/1924 | Behan . |
| 2,382,276 | 8/1945 | Wells . |
| 2,490,969 | 12/1949 | Kinyon . |
| 3,122,139 | 2/1964 | Jones, Jr. . |
| 3,259,920 | 7/1966 | Voller . |
| 3,339,551 | 9/1967 | Stoutenburgh ............... 604/349 |
| 3,750,648 | 8/1973 | Gleason et al. . |
| 3,835,857 | 9/1974 | Rogers et al. ............... 604/349 |
| 4,134,512 | 1/1979 | Nugent ........................ 128/764 |
| 4,239,044 | 12/1980 | Pavlinch ...................... 128/760 |
| 4,296,502 | 10/1981 | Bortle . |
| 4,349,035 | 9/1982 | Thomas et al. .............. 128/766 |
| 4,378,018 | 3/1983 | Alexander et al. .......... 128/760 |
| 4,475,909 | 10/1984 | Eisenberg ................... 128/760 |
| 4,656,675 | 4/1987 | Fajnsztajn ................... 128/767 |
| 4,790,834 | 12/1988 | Austin ........................ 128/767 |
| 4,846,819 | 7/1989 | Welch . |
| 4,895,167 | 1/1990 | Guala ......................... 128/760 |
| 4,963,137 | 10/1990 | Heyden ...................... 604/349 |
| 5,257,984 | 11/1993 | Kelley ........................ 128/764 |
| 5,267,989 | 12/1993 | Moyet-Ortiz ............... 128/760 |

*Primary Examiner*—Max Hindenburg
*Attorney, Agent, or Firm*—Charles G. Lamb; Middleton & Reutlinger

[57] ABSTRACT

A device for collecting uncontaminated urine specimens from adult females, adult uncircumcised males and pediatric males. The device includes an elongated flexible tubular conduit member having a funnel-shaped opening at one end to be in sealing relationship with a urethra or glans penis and a discharge end to be received within a sample container. The sample container includes an opening with sealing means therein to receive the discharge end of the elongated flexible tubular conduit member in an open position to receive a urine specimen and in a closed position when the discharge end of the elongated flexible tubular conduit member is withdrawn.

9 Claims, 3 Drawing Sheets

URINE SPECIMEN COLLECTION DEVICE

This is a divisional application from U.S. patent application Ser. No. 08/149,549, filed Nov. 9, 1993 now abandoned.

BACKGROUND OF THE INVENTION a) Field of the Invention

This invention relates to the collection of urine specimens from patient groups including adult females, adult uncircumcised males, and pediatric males.

b) Discussion of the Prior Art

Medical science has proven the need for routine urinalysis to detect enumerable disease processes. The most commonly used method for this in the hospital, office practice and home health practice, is a clean catch mid-stream urinalysis. The clean catch mid-stream urinalysis is currently collected in one of many different size cups or containers. However, it has been found that adult females, adult uncircumcised males, and pediatric males have specific and distinct problems in relation to the presently used collection methods. For example, in the adult female, vaginal voiding and contamination by the labia and hair of the vaginal region during the act of micturition renders many of the urinalyses unusable in relation to accurate bacterial and leucocyte quantifications. In present practice this necessitates the insertion of a tube into the bladder for an accurate urinalysis when looking for an infection. In the adult uncircumcised male, for example, often this person is not instructed in the proper collection of the specimen (pulling the foreskin back and cleansing the glans penis) and therefore contamination occurs. Also, for example, in the neonatal and young pediatric male, collection devices are generally a bag-like device placed around the scrotum, penis, and suprapubic region, thereby enhancing bacterial contamination.

There have been a number of suggestions for apparatuses for taking urinary samples in the prior art, but none have found acceptability in the medical profession involved with overseeing the taking of samples and transporting said samples for analytical evaluation. One particular reference noted is U.S. Pat. No. Re. 26,854 which teaches an apparatus for collecting urine samples from female patients which includes a container with an elongated tube sealingly mounted in the open end of the container. The elongated tube on its distal end includes a compressible and resilient pad portion which is adapted to be positioned around the urethral meatus and in use the urine is collected in the sample collector.

SUMMARY OF THE INVENTION

Accordingly, it is a principal object of the present invention to provide an apparatus for improving the collection of urine samples from adult females, adult uncircumcised males, and pediatric males and subsequently decreasing contamination of the samples.

It is another object of the present invention to provide an apparatus for the collection of urine samples which reduces the number of contaminated urine samples obtained from adult females, adult uncircumcised males and pediatric males and subsequently decreasing contamination of the samples.

It is even another object of the present invention to provide an apparatus for the collection of urine specimens to reduce the number of patients being treated unnecessarily for urinary tract infections due to contaminated urine specimens.

It is an even further object of the present invention to provide an apparatus for the collection of urine specimens and reduce the time spent in the transfer of the urine from the collection device by lab or office personnel.

It is an even further object of the present invention to provide a collection device of urine specimens which reduces certain unnecessary health care expenditures due to the rerunning of urinalyses due to contamination in obtaining the samples.

An even further object of the present invention is to provide a urine specimen collection device which includes means to form a tight seal around the female urethra and urethra of the male glans penis to reduce extra urethral contamination.

Also an object of the present invention is to provide a device for taking urine samples which is simple, rapid and eliminates the need for transferring urine from a cup or bag to a centrifuge tube.

It is even a further object of the present invention to provide a system whereby a health care attendant or the patient can see when a centrifuge tube is filled and includes means to remove it before overflow occurs. An even further object of the present invention is to provide an apparatus for use with a pediatric male to allow the device to be taped to the glans penis until a urine specimen is collected.

More particularly, the present invention provides a device for collecting urine samples comprising:

an elongated flexible tubular conduit having a funnel-shaped first opening at one end and a second opening at the opposite end, said funnel-shaped opening being sized to fit around the outer periphery of a urethral meatus and to form a seal thereabout;

a sample collector having an opening therein; and, a plug disposed within said opening of said sample collector, said plug having means to receive said opposite end of said tubular conduit therethrough, said means to receive said opposite end of said tubular conduit including sealing means when not in receipt of said opposite end therein.

Accordingly, other objects, features and advantages of the present invention will be apparent by reference to the following description of preferred embodiments, drawings and claims.

BRIEF DESCRIPTION OF THE DRAWINGS

A better understanding of the present invention may be obtained from the following detailed description of the preferred embodiments described in connection with the accompanying drawings wherein.

DETAILED DESCRIPTION OF THE PREFERRED EMBODIMENT

Figure 1:
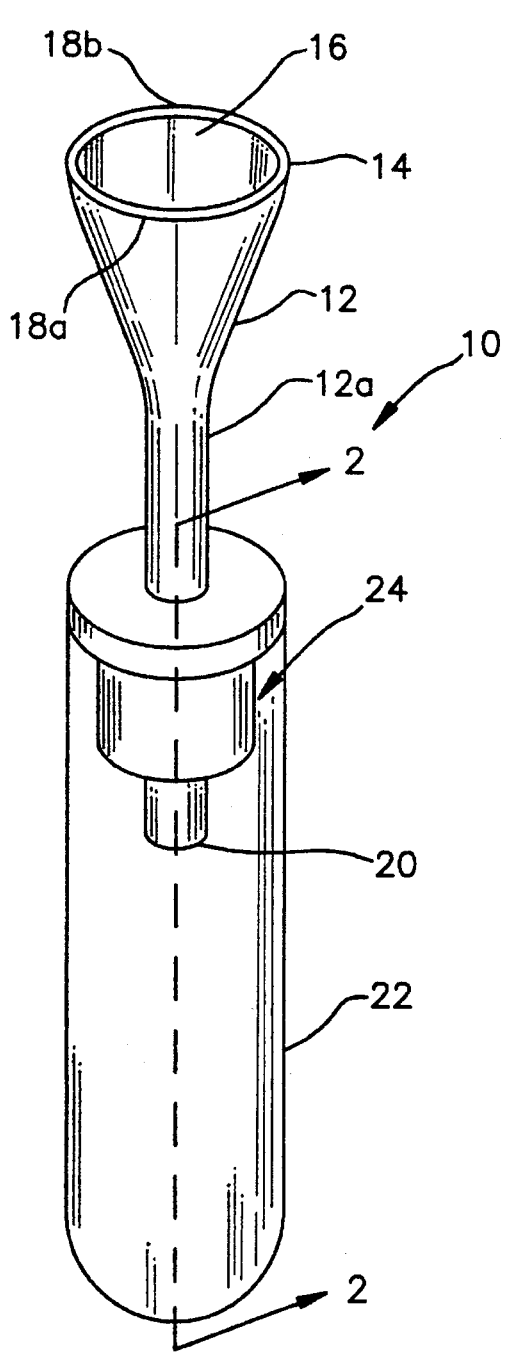
FIG. 1 is a perspective view of one preferred urine collection device of the present invention.

Referring now to the drawings, as best shown in FIG. 1, a urine sampling device 10 comprises a flexible tubular conduit member 12, a closure 24 and a sample collector 22.

The flexible tubular conduit member 12 is provided with a funnel-shaped end 14 and a discharge end 20. Between the funnel-shaped end 14 and the discharge end 20 is a flexible tubular portion 12a.

Figure 6:
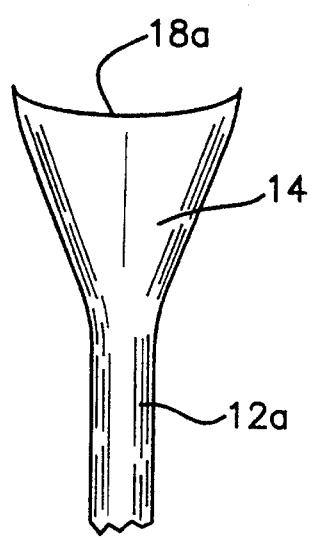
FIG. 6 is a side view of the funnel-shaped opening of the elongated flexible tubular conduit member shown in FIG. 1.
Figure 7:
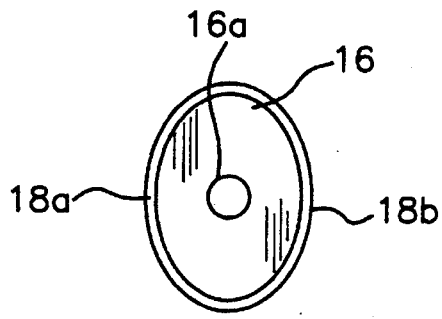
FIG. 7 is a top view of the funnel-shaped opening of the elongated flexible tubular conduit member shown in FIG. 1.

The funnel-shaped end 14 of the flexible tubular conduit member 12, as best shown in FIGS. 6 and 7, includes an elliptically-shaped opening 16 with concave-shaped sides 18a and 18b, and an opening 16a which provides means for the flow of fluid from the funnel-shaped end 14 into the flexible tubular portion 12a. However, it is realized that the opening 16 may be circular-shaped, and include fastening tabs 42 on each side thereof (FIG. 9) for attaching and holding the conduit member 12 onto the penis of a pediatric male.

Figure 2:
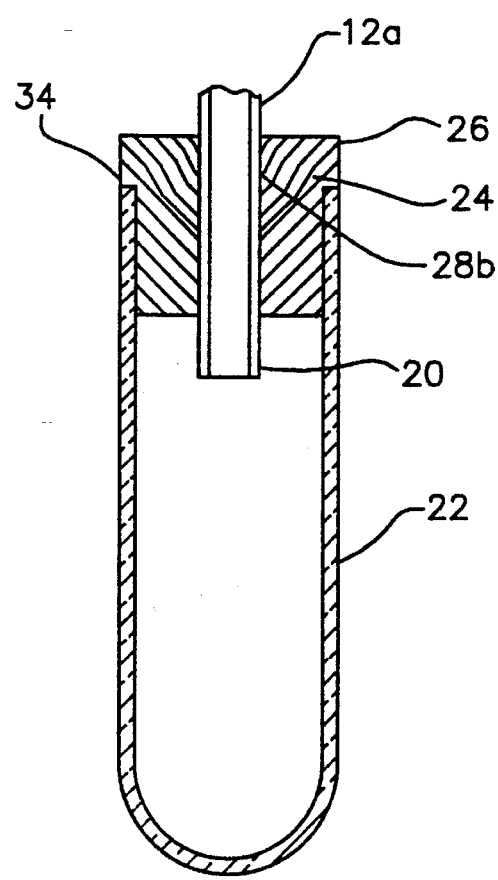
FIG. 2 is a cross-sectional view taken along line 2—2 of FIG. 1.

As best shown in FIG. 2, the sample collector 22 is provided with an opening 34 therein to receive the closure member 24.

The closure member 24, as shown in FIGS. 2, 3, 4 and 5 is in one preferred embodiment shown as being cylindrically-shaped of T-shaped cross-section including a first cylindrical disc portion 26 unitary with a second cylindrical disc or valve portion 28 wherein said first disc 26 is of a greater diameter than said second disc 28. The first disc portion 26 covers the opening 34 in the sample collector 22. The cylindrically-shaped valve portion 28, which is generally made of a resilent elastomeric material, has an outer diameter substantially the same as the inner diameter of the opening 34 of the sample collector 22, so that upon insertion into the opening 34, the closure member 24 is in sealing relation with the sample collector 22 so the fluid collected within the sample collector 22 is maintained therein.

Figure 3:
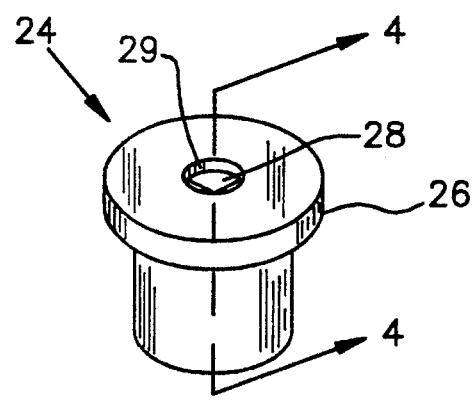
FIG. 3 is a perspective view of a closure member of the preferred embodiment as shown in FIG. 1.
Figure 4:
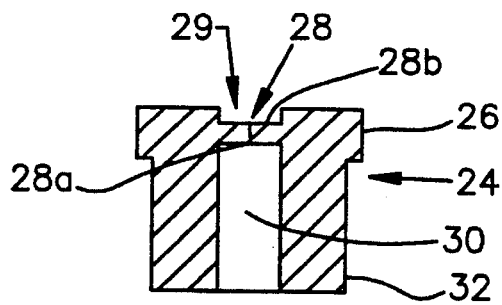
FIG. 4 is a cross-sectional view taken through line 4—4 of FIG. 3.
Figure 5:
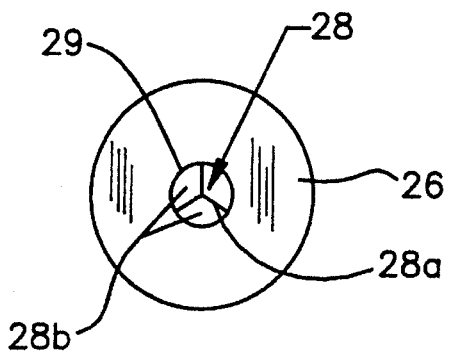
FIG. 5 is a top view of the closure member of FIG. 3.

As shown in FIGS. 3, 4 and 5, the closure member 24 also includes a centrally disposed opening 29 in the first disc portion 26 which is in flow communication with passageway 30 which is disposed centrally of the closure member 24. The opening 29 and the passageway 30 are in axial alignment and are sized with an inner diameter substantially the same as the outer diameter of the flexible tubular portion 12a of conduit member 12. The valve 28 is generally unitary with the first disc 26 and in one preferred embodiment includes three radial slits 28a which are equally spaced around the valve portion 28. And, the slits 28a extend completely between the opening 29 and the passageway 30 defining three pie-shaped vertical sections 28b therebetween.

Figure 8:
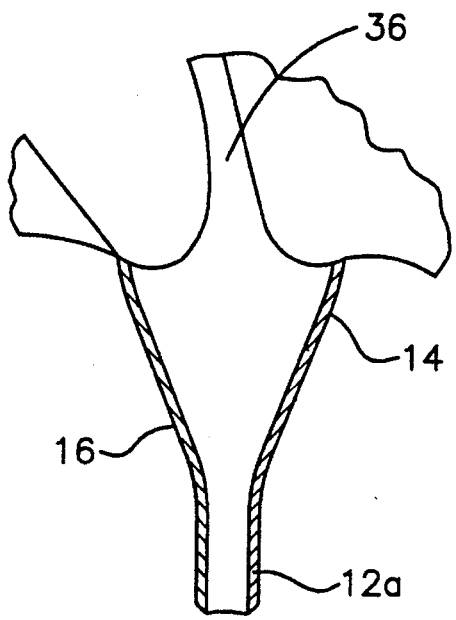
FIG. 8 illustrates by a cross-sectional view of the funnel-shaped end of the elongated conduit member of FIG. 4 in a use position with the urethra of a female and shows how the device is used to obtain urine samples; and, FIG. 9 illustrates by an enlarged cross-sectional view of another funnel-shaped end of an elongated conduit member in a use position with the glans penis of a pediatric male.

As shown in FIG. 8, the funnel-shaped end 14, having an elliptically-shaped opening 16, is sized to fit over and in sealing relationship with the urethra 36 of an adult female.

Figure 9:
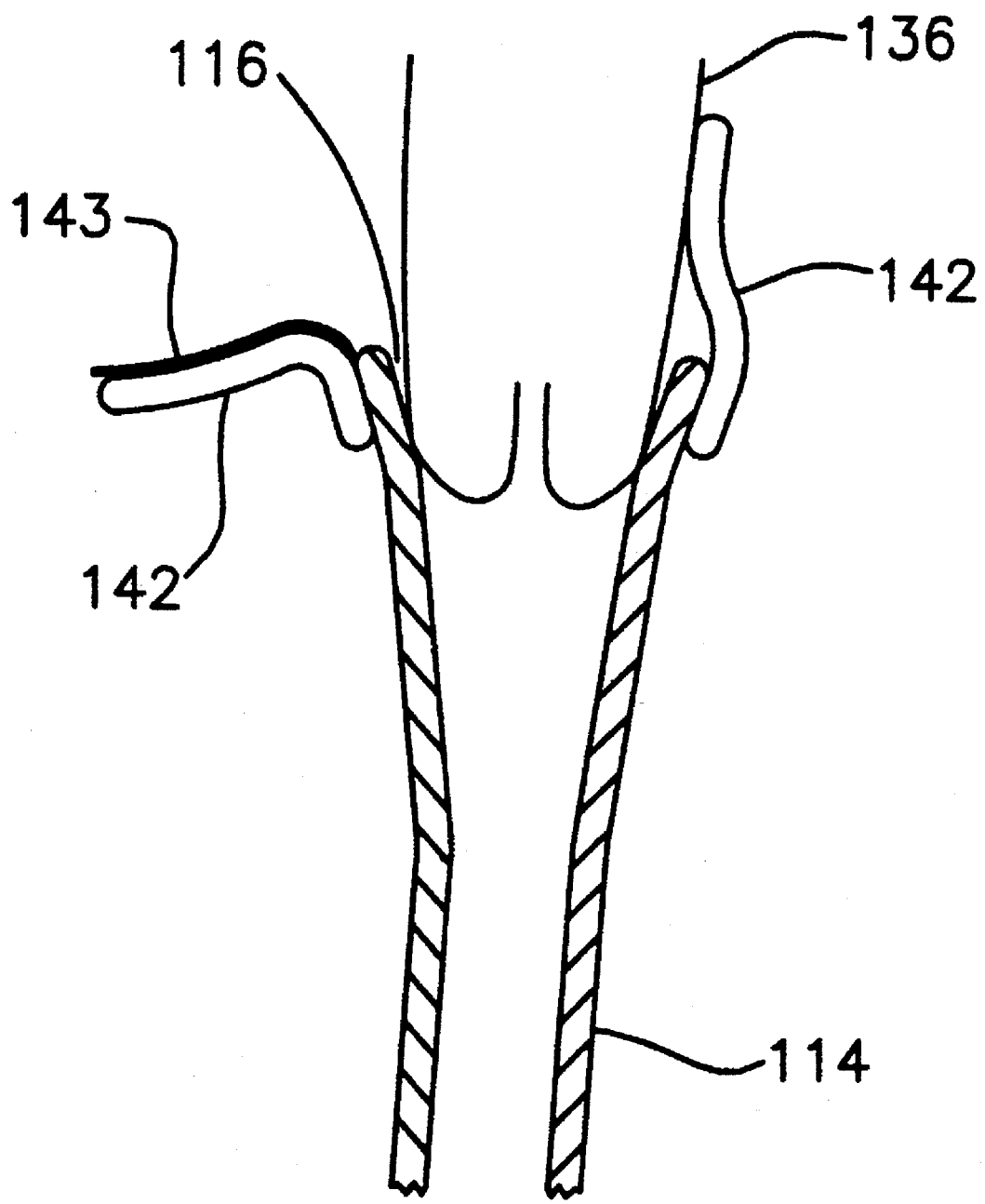

As shown in FIG. 9, the funnel-shaped end 114 is provided with a circularly-shaped opening 116 which is sized to fit the urethra of a glans penis 136 of an uncircumsized male and a pediatric male. For pediatric males, fastening tabs 142 are provided for attaching the end 114 to the glans penis 136 of the pediatric male. Fastening tabs 142 are shown as a pull back tape well known in the art having a backing 143 thereon. When attaching, backing 143 is pulled back and the tape portion 142 is attached to the glans penis 136 and held thereon until a sample is received.

In operation, the sample collector 22 which is usually a centrifuge tube, is provided with a closure 24 disposed within the opening 34 in sealing relationship with the interior of the semptecollector 22. The funnel-shaped end 14 of the flexible tubular conduit member 12, is then positioned as shown in FIG. 8 over the urethra 36 of an adult female and the discharge end 20 of the flexible tubular conduit 12 is inserted within the plug 24. The end 20 is pushed through the valve portion 28 wherein the slits 28a yield to the tubular portion 12a passing therethrough. The slits 28a define vertical substantially pie-shaped sections 28b which fold down and back against themselves and the inner walls of the passageway 30 thereby allowing the passage of the discharge end 20 therethrough. The discharge end 20 extends a preselected distance beyond the end of the plug 24, as shown in FIG. 2. The urine specimen is then deposited into the centrifuge tube and upon completion of the collection of the urine specimen, the discharge end 20 of the flexible tubular conduit member 12 is then removed from the closure member 24 and the valve 28 is resealed as the vertical sections 28b returns to their normal positions. Thus, the sample collector 22 is then sealed by the return of the valve portion 28 to its closed position and the centrifuge tube 22 is then taken away for analysis.

It is realized that other variations and modifications of the preferred embodiment are possible without departing from scope and spirit of the present invention. And, it is not intended that the aforementioned discussion in any way limits the scope of the present invention as set forth in the appended claims.

What is claimed is:

1. A device for collecting urine samples comprising:

an elongated flexible tubular conduit having a funnel-shaped first opening at one end and a second opening at the opposite end, said funnel-shaped opening being sized to fit around the outer periphery of a glans penis and to form a seal thereabout; said tubular conduit member includes fastening tabs thereon for attaching said tubular conduit member to a glans penis;

a sample collector having an opening therein; and, a closure member disposed within said opening of said sample collector, said closure member having means to receive said opposite end of said tubular conduit therethrough, said means to receive said opposite end of said tubular conduit including sealing means when not in receipt of said opposite end therein.

2. The device of claim 1 wherein said funnel-shaped opening is provided with a circular-shaped opening.

3. The device of claim 1 wherein said sample collector is a centrifuge tube.

4. The device of claim 1 wherein said closure member is a plug having an outside diameter substantially the same as the inside diameter of said opening in said sample collector, said plug having a valve portion therein, said valve portion receiving said opposite end of said elongated flexible conduit member in one position and being in a closed position when not in receipt of said opposite end of said elongated flexible conduit member.

5. The device of claim 4 wherein said plug is provided with a first cylindrical disc portion and a second cylindrical disc portion, said first cylindrical disc portion having a greater diameter than said second cylindrical disc portion.

6. The device of claim 5 wherein said first cylindrical disc portion is provided with a centrally disposed opening therethrough, said centrally disposed opening having a diameter substantially the same as the outside diameter of the opposite end of said elongated flexible tubular conduit member.

7. The device of claim 6 wherein said second cylindrical disc portion is provided with a centrally disposed passageway therein in alignment with and of the same diameter as said centrally disposed opening of said first cylindrical disc portion.

8. The device of claim 7 including a valve portion disposed between said opening of said first cylindrical disc portion and said passageway of said second cylindrical disc portion.

9. The device of claim 8 wherein said valve portion is of an elastomeric material and includes three slits therein, each slit extending from said opening of said first cylindrical disc on one end and said passageway on said opposite end, each of said slits being disposed substantially equal distances apart defining three vertically extending pie-shaped portions therebetween whereby said valve portion is capable of receiving said opposite end of said elongated flexible tubular conduit member therethrough in a receiving position and in a sealing position when not in receipt of said opposite end of said elongated flexible tubular conduit member.

* * * * *